United States Patent [19]

Vilkomerson et al.

[11] Patent Number: 5,076,278
[45] Date of Patent: Dec. 31, 1991

[54] ANNULAR ULTRASONIC TRANSDUCERS EMPLOYING CURVED SURFACES USEFUL IN CATHETER LOCALIZATION

[75] Inventors: David Vilkomerson, Princeton; Bayard Gardineer, Skillman; Francis A. Debernardis, Jr., Ridgewood, all of N.J.

[73] Assignee: Catheter Technology Co., North Brunswick, N.J.

[21] Appl. No.: 597,508

[22] Filed: Oct. 15, 1990

[51] Int. Cl.$^5$ .............................................. A61B 8/00
[52] U.S. Cl. ............................... 128/662.03; 73/861.25
[58] Field of Search ..................... 128/662.03, 662.06; 73/861.25

[56] References Cited

U.S. PATENT DOCUMENTS

| 3,938,502 | 2/1976 | Bom ............................ | 128/662.06 |
| 4,354,502 | 10/1982 | Colley et al. ................ | 128/662.06 |
| 4,665,925 | 5/1987 | Millar ......................... | 128/662.06 |
| 4,815,470 | 3/1989 | Curtis et al. ................. | 128/662.03 |
| 4,947,852 | 8/1990 | Nassi et al. .................. | 128/662.06 |

Primary Examiner—Francis Jaworski
Assistant Examiner—George Manuel
Attorney, Agent, or Firm—Arthur L. Plevy

[57] ABSTRACT

An ultrasonic transducer for use in locating devices with an ultrasonic imaging system which is sensitive over a broad range of angles of incident acoustic beams, such as those beams emitted in ultrasonic systems, has a curved surface, and is an annular member in shape. The elongated catheter or other device passes through the opening of the annular transducer. Based on the shape of such transducers and the wavelength used, the response of the transducers is a function of the angle of the insonifying beam to the catheter axis. The particular response of such transducers is shown to depend on the curvature of the annular marker, with the radius of curvature chosen on the basis of the wavelength used in the ultrasonic scanning system; between 2-50 wavelengths.

20 Claims, 4 Drawing Sheets

ANNULAR ULTRASONIC TRANSDUCERS EMPLOYING CURVED SURFACES USEFUL IN CATHETER LOCALIZATION

FIELD OF INVENTION

This invention relates to ultrasonic imaging systems and more particularly to an annular ultrasonic transducer employed for accurately locating the position of a catheter.

BACKGROUND OF THE INVENTION

As one can ascertain, there are many medical procedures where the knowledge of the position of a catheter is desirable. One such example is in positioning a balloon angioplasty catheter. In such a system one portion of the catheter utilized expands upon inflation thereby opening up a narrow section of an artery which artery contains plaque. The objective is positioning the catheter so that the balloon portion is where the plaque is. According to present techniques of providing such positioning, one employs X-ray fluoroscopy. In X-ray fluoroscopy a contrast agent which is visible under X-ray radiation is sent through the catheter and its tip and is made visible by the use of X-ray fluoroscopy. Such methods of positioning a catheter and other interventional systems employ X-ray techniques to locate the position of the catheter within the body cavity. As one can understand, the drawbacks of X-ray visualization include the potential harmful effects of the radiation to the patient and attending physicians. There is potential for additional harmful effects due to the contrast agent. Another major concern is the cost of the X-ray apparatus and personnel.

Certain other prior art techniques utilize highly radiopaque tantalum or other metal markers which identify the area of effective dilatation. These tantalum markers are firmly anchored on the catheter shaft to enable one to detect the position of the catheter by means of X-ray.

The prior art was cognizant of the harmful effects of X-ray radiation and hence, prior art approaches attempted to utilize ultrasound or other imaging techniques which were well suited for soft tissue analysis and which techniques presented no X-ray hazard. In this regard, reference is made to U.S. Pat. No. 4,249,539 entitled ULTRASOUND NEEDLE TIP LOCALIZATION SYSTEM issued on Feb. 10, 1981 to D. H. R. Vilkomerson, et al. This patent describes a system which detects the tip of an aspiration needle used in an aspiration procedure and shows the tip in an ultrasound image by means of a transducer removably positioned at the tip. The patent describes utilizing the transducer as a transponder and thereby sending a signal back through the body to the transmitter when a signal is detected. In the patent, the aspiration needle removably carries a small, omnidirectional ultrasound transducer which is electrically connected through the needle to transponder electronics. Incident pulses from the imaging transducer to the hemispherical transducer at the needle tip are sensed at the latter and the aspiration needle position is inserted into the image either by generation of a return signal emitted from the needle point, "direct transponding" or by sending an appropriately delayed signal directly to the transmitting system via a wire rather than through the body "indirect transponding".

Reference is also made to U.S. Pat. No. 4,706,681 entitled CARDIAC ULTRASONICALLY MARKED LEADS AND METHOD FOR USED SAME issued on Nov. 17, 1987 to B. Breyer, et al. This patent describes ultrasonically marked leads produced by mounting one or more piezoelectric marker transducers into the leads and connecting the transducers by electrical conductors to appropriate electric circuits which upon reception of the scanner ultrasonic signals by the marker transducers generate appropriate electric signals. These signals localize the marker transducers in an ultrasonic echographic image, thereby permitting guiding of pacing leads and detection of malfunctions.

As one can see from this patent, the marker transducers are cylindrical or tubiform in shape. These transducers are flat in regard to their surface configuration and in all cases the cylinders are longer than the diameter. In some cases the cylinders are twice as long as the diameter to conform to the definition of tubiform. Such tubular transducers are sensitive only to beams that are close to perpendicular to their long axis. As will be further explained, the angle over which such a transducer has significant sensitivity is extremely small.

The tubiform transducers shown in U.S. Pat. No. 4,706,681 are incapable of responding to energy which impinges from angles other than energy directed perpendicular to the axis of the transducer. As will be described, such transducers can not be used to reliably locate the position of a catheter. The hemispherical transducer of 539 cannot be mounted on the tubular portion of a catheter.

The present invention, a curved annular transducer, circumvents the prior art problems: the transducer to be described is both sensitive over a broad range of angles of incident acoustic beams, and mountable on a tube in any required location. In this manner, it enables an ultrasonic imaging system to show the position of the transducer on a tubular device during normal scanning modes.

SUMMARY OF THE INVENTION

A transducer for use with a scanning ultrasonic imaging system to enable the location of a catheter associated with the transducer by said system comprising an annular member having a curved outer surface having a radius of curvature in the plane to be scanned between 2 to 50 wavelengths of the ultrasonic frequency employed in said imaging system.

DETAILED DESCRIPTION OF THE INVENTION

Figure 1:
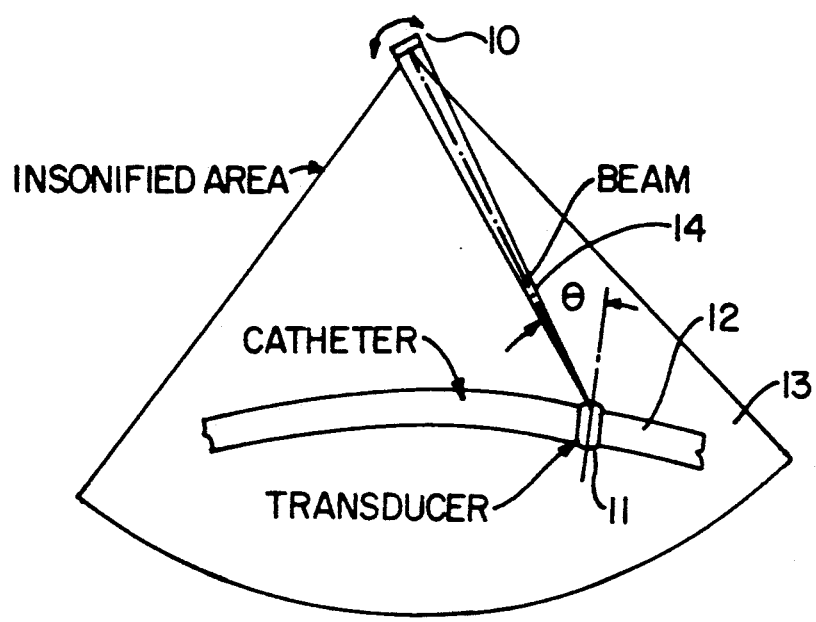
FIG. 1 is a schematic view depicting an ultrasonic scanning head radiating onto a transducer according to this invention.

As shown in FIG. 1, there is a ultrasonic scanning transducer 10 which scans in a well known manner to produce an insonified area 13. A catheter 12 is directed into the body of a patient and for example, in the case of an angioplastic technique, would be directed into a suitable artery or vessel. The catheter would then be positioned or moved by a surgeon or other practitioner to a desired location. As indicated above, a primary concern of the physician is to determine where the catheter is. Associated with the catheter is a transducer element 11 which as will be explained is the subject matter of this invention. The transducer has a coating on a surface thereof which is piezoelectric. The transducer 11 is an annular member with curved outer surfaces.

As seen in FIG. 1, a beam 14 which emanates from the scanning transducer 10 impinges upon the surface of the transducer 11. The transducer 11 is characterized in having a curved outer surface with the central aperture encircling the catheter 12 and positioned near the tip. The key to the use of the transponding technique is insuring that the transducer 11 is sensitive over a broad range of angles of incident acoustic beams. As the location of the localizing transducer 11 can be anywhere in the acoustic field 13, it must respond to beams in the plane of scanning 13 coming in at an angle far from the perpendicular to the catheter axis. If this is not so, the localizing transducer 11 will be invisible unless it is directly under the transmitting scanner 10. In that situation, the ordinary catheter is visible as well since under perpendicular insonification strong reflections are obtained.

Figure 2:
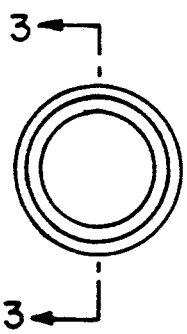
FIG. 2 is a front plan view of transducer according to this invention.

In the prior art such as in U.S. Pat. No. 4,706,681, the transducers shown do not meet this requirement. The marker transducers shown in the 681 patent are basically cylindrical or tubiform in shape. The drawings as well as the text depicts such transducers which are flat and in all cases the cylinders are longer than the diameters as indicated above. Such Tubular transducers are sensitive only to beams that are close to perpendicular to the long axis (see Appendix). As shown in FIG. 2 of the appendix, only within the angle a' defined by the following equation:

$$a' = \arcsin \frac{\text{wavelength}}{\text{tubelength}}$$

is a tubular transducer sensitive. Thus, as one can see a tubular transducer is sensitive only to beams that are close to perpendicular to the long axis, i.e., only within the angle a' is such a tubular receiver sensitive. In order to analyze the range of angular sensitivity of the transducer, as for example described in U.S. Pat. No. 4,706,681, it is assumed operation is at the usual imaging frequency of 7.5 MHz. The wavelength is 0.2 millimeters. The tubelength is at least two mm long, as that is the diameter of a small catheter, and the tubelength is at least this diameter in size. Hence, the angle over which such a transducer has significant sensitivity, as given by the above equation is less than ±9 degrees. As the usual ultrasound image covers ±45 degrees, such a transducer would mark its location only in the central 20% of the image.

Figure 3:
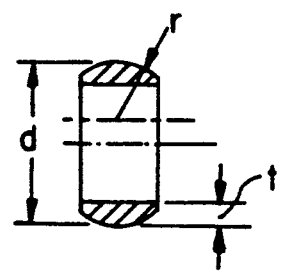
FIG. 3 is a cross sectional view of the transducer taken through line 3—3 of FIG. 2.

Referring to FIG. 2 and FIG. 3, there is respectively shown a front plan view of a curved angular transducer according to this invention. It is shown curved in both dimensions so that the sensitivity is independent of its rotation around its long axis; this is the usual case, but the transducer may be asymmetrical, for example, to allow for rotational orientation of the catheter for positioning means. In a similar manner, by selectively plating the transducer we can obtain rotational asymmetry. Accordingly, the transducer may have only a portion of its surface curved, with the remaining portion of the surface being flat. The curved portion has a radius of curvature which is a function of the frequency employed in the ultrasonic system, as will be explained. In this manner, the curved portion will detect the ultrasonic rays much more efficiently than the flat portion. Therefore, if the transducer is placed on a catheter, one could then rotate the catheter to determine rotational position based on the effective curved surface portion of the transducer. This may be for mechanical or laser angioplasty where rotational orientation may be important. FIG. 3 shows a cross sectional view of the transducer taken through line 3—3 of FIG. 2. The curved angular transducer is employed for ultrasonic catheter localization. The transducers are characterized essentially by three parameters.

The transducer has a total diameter as shown in FIG. 2 designated as d. The transducer has a radius of curvature along the catheter axis designated as r and a curved section which occupies thickness t. The actual thickness of the transducer layer is on the order of multiple-quarter wavelengths of the ultrasound in the transducer, as is well known in the art (see "ULTRASOUND TRANSDUCERS FOR PULSE-ECHO MEDICAL IMAGING" by J. W. Hunt, et al, IEEE BME-30, 453 (1983).

As discussed in the Appendix, the response as a function of angle of the insonifying beam to the catheter axis of such transducers depends on the radius of curvature and wavelengths used.

Figure 6:
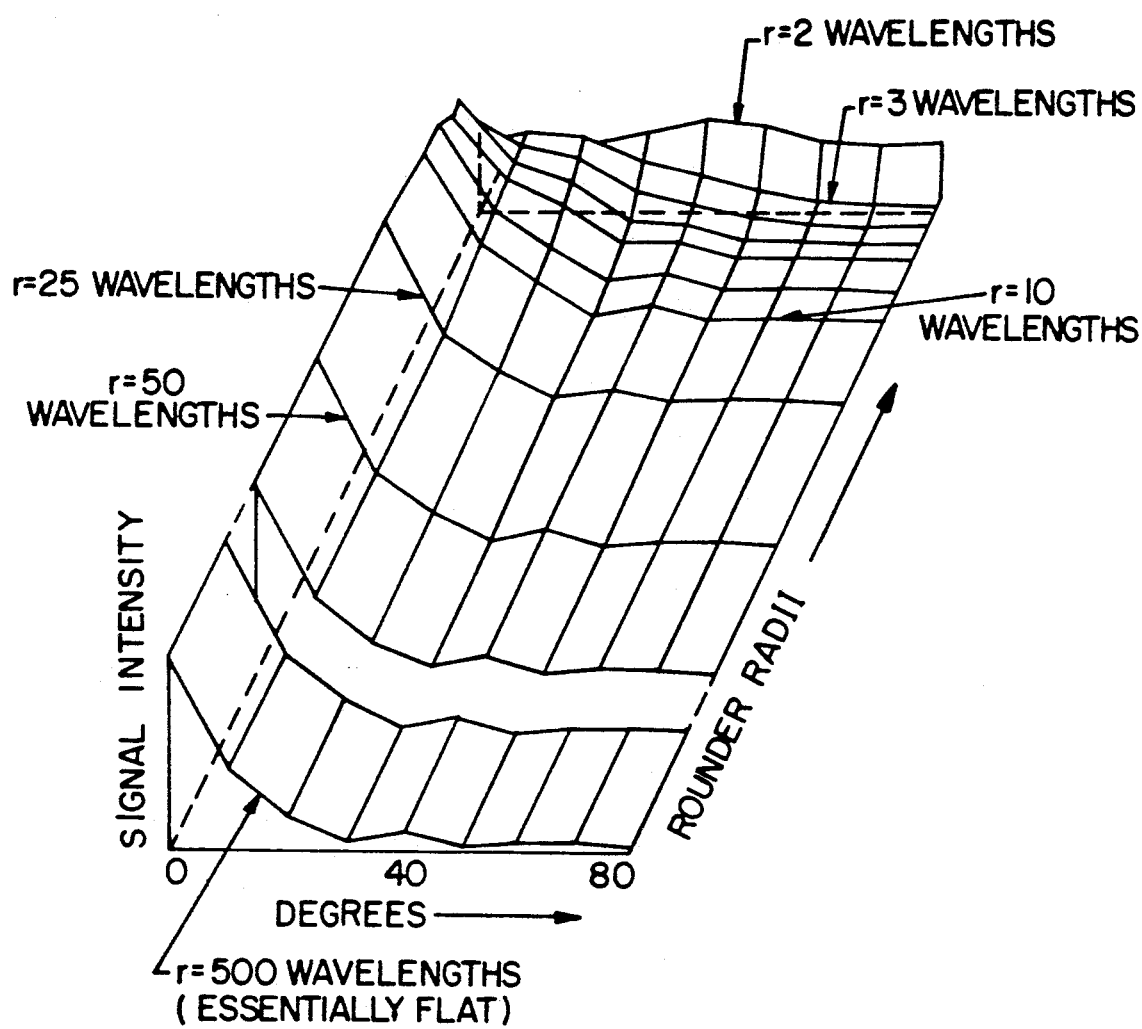
FIG. 6 is a graph depicting transducer operation according to this invention.
Figure 7:
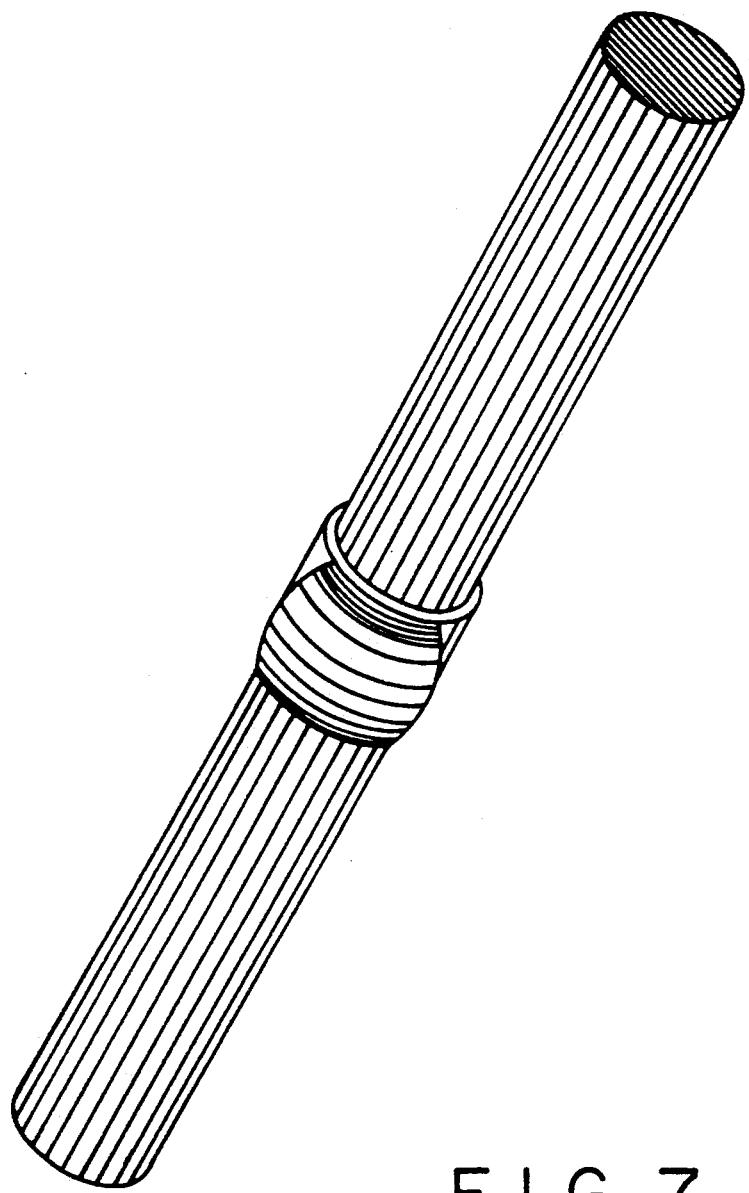
FIG. 7 is a perspective plan view of a transducer according to this invention including an assymetrical surface.
Figure 8:
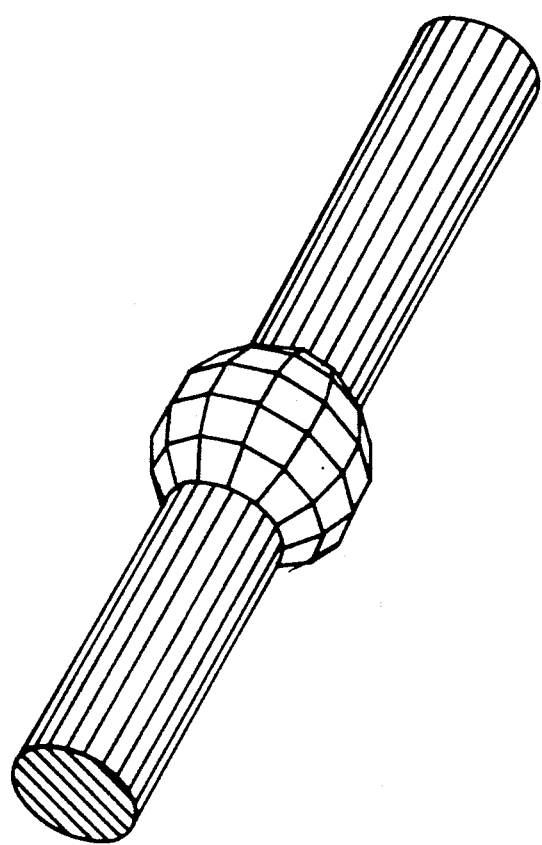
FIG. 8 is a perspective plan view of a transducer according to this invention including a multiplicity of facets that approximates a smooth curved surface.

In FIG. 6, there is shown a response for curved-ring transducers with varying radii of curvature calculated by using the equations shown in the Appendix. For reference, it is shown that the response of a flat ring of comparable width is much narrower, making it unusable for catheter location as discussed above. The curved-ring transducers, in contrast, can be designed to have usable sensitivity beyond 60 degrees. There is some trade-off in sensitivity compared to the flat transducer at zero angle, but at 60 degrees, for example, the curved transducer is fifty or more times as sensitive as a flat transducer.

The particular shape of these transducers, for example, the curved rings or annular curved transducers is calculated from the equations contained in the Appendix. However, in general, transducers having curved surfaces rather than flat tubes are disclosed. The radius of curvature, the thickness of the transducer, and the catheter diameter determine the shape of the transducer. As shown in the Appendix, useful shapes of such transducers may be made with radii of curvature between 2 and 50 wavelengths; using the equations in the Appendix, the appropriate curvature for a particular imaging situation may be calculated.

Approximations to the curved ring for example, a multiplicity of facets or bevels employed on the surface of such a catheter would also increase the range of angular acceptance.

Thus, there has been disclosed a technique including design criteria for transducers placed on a catheter allowing them to be located with accuracy by a scanning ultrasound imaging system. As one can understand, the ultrasound imaging system as described will respond as a transponder, either directly or indirectly (as has been described) to ultrasonic waves which impinge on the surface of the catheter as, for example, depicted in FIG. 1.

Figure 4:
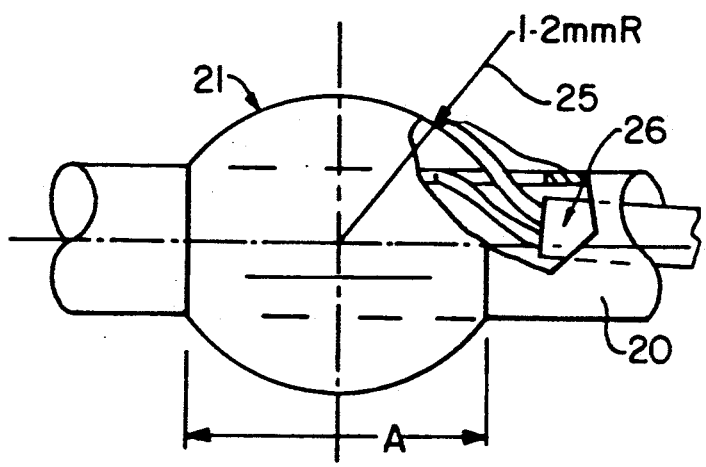
FIG. 4 is a side plan view of transducer according to this invention.
Figure 5:
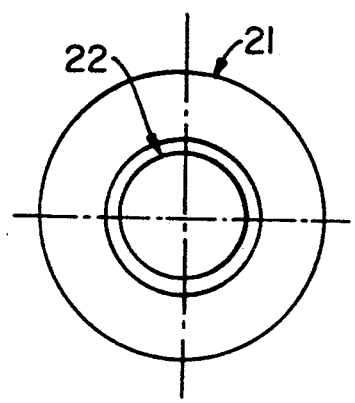
FIG. 5 is a front plan view of the transducer shown in FIG. 4.

Referring to FIG. 4 and FIG. 5, there is shown a side and front view of an annular transducer which can be employed with an ultrasonic scanning system according to the present invention. Essentially, the transducer is placed over a tube or catheter 20. The transducer surface 21 is fabricated from a suitable piezoelectric material or piezoelectric alloy and as seen has a definite curved surface. The length of the transducer as designated by reference numeral A is 2 mm. The diameter of the hole 22 is 1 mm which essentially is the diameter of the tube 20. The transducer has a radius which is indicative of the surface configuration and which is directed from the center line of the catheter axis of 1.2 mm. This is designated in the figure by the line associated with arrow 25. The 1.2 mm radius of curvature is indicative of 6 wavelengths at 7.5 MHz which is a typical frequency employed in ultrasonics. Essentially, the catheter is located by means of the scanning head of the ultrasonic system which emits rays and which rays will impinge on the curved surface of the transducer to thereby accurately locate the catheter. The transducer is coupled to the cable 26 which may be a two wire cable. The cable 26 is operative to receive the pulses of transducer 11 for either direct transponding mode, by applying an ultrasonic pulse to the transducer, or by indirect transponding mode. Means of locating the catheter based on the transponded pulses can be implemented in many different ways as can be ascertained by one skilled in the art.

APPENDIX

Introduction

In this Appendix, we teach how to calculate the response of a piezo-responding material when used on a curved surface as a transducer for ultrasonic waves, such as for the use disclosed in the patent to which this is attached. The method of calculation is general, showing what curvatures produce what response. In particular, we will calculate the response for a spherical-surface ring transducer as disclosed, the response for a tubular transducer that appeared in a previous patent, and indicate the method of calculation for other kinds of curved-surface transducers.

The Method

A piezoelectric material converts pressure into voltage, positive pressure a positive voltage and negative pressure (i.e. below ambient average) a negative voltage. For simple uniform constant force this voltage is easy to calculate.

For an ultrasonic wave travelling through space at some angle to an arbitrarily curved surface, it is not so easy. The pressure is different from one moment to the next and from one point to the next. We can easily imagine a positive voltage, caused by a "crest" in pressure at one point on the transducer, being simultaneously cancelled out by a negative voltage produced by a "trough" of pressure at another point.

We must find the phase relationship of the ultrasonic pressure waves hitting the transducer to determine the overall voltage generated (see, for example, FIG. 1). We can find the *relative* phases by finding the differences in path length between a wavefront (locus of points of equal phase) and the points on the transducer. We can then examine how the overall voltage changes in time as these phases vary together over one cycle.

By varying the angle of the impinging ultrasonic beam, we can plot out how the sensitivity of the transducer varies with the angle of the impinging beam and the shape of the transducer. With this information, we can design the shape of the transducer that is needed to carry out the locating function of the attached patent.

The Flat Transducer

We will first demonstrate the method on a particularly simple "curved" surface: a flat plate (equivalent to a curved surface whose radius of curvature is infinite).

As shown in FIG. 1, we assume a beam of width $2x_o \cos a$, with flat wavefronts, which is the shape of wavefronts in the region of focus. We say the beam hits the plate at an angle a, as shown, and the reference wavefront crosses the point $x = 0$ at time $t = 0$.

The general form for the pressure as a function of time and space of an ultrasound wave of frequency f and propagation velocity c is $$p = p_{max} \cdot \cos 2\pi f(t + d/c) \qquad (1)$$

where d is the distance travelled from some reference and t is the time from 0. (If you examine this equation, you see that if you look at one spot, the pressure goes through a cycle every $t = 1/f$ seconds, and if you look at one instant of time, as we are doing in FIG. 1, the pressure goes through one cycle every $d = f/c$ distance; since the velocity equals the frequency times the wavelength, f/c is exactly the spatial wavelength.)

Looking at FIG. 1, we can calculate the distance from the reference wavefront to the transducer on the x-axis. Each of the lines perpendicular to the wavefront form a right triangle whose apex angle is a and whose hypotenuse is x. Therefore, $$\Delta L = -X \cdot \sin a, \qquad (2)$$

where the minus sign shows that for positive x the distance from the reference wavefront is negative.

We note that the way we have chosen our reference wavefront, at $x = 0$ we have $\Delta L = 0$.

We can now say that at $t = 0$ the pressure of the wave as it strikes the x-axis (as a function of x and using (1)) is $$p(x) = p_{max} \cdot \cos 2\pi f(\Delta L/c), \qquad (3)$$

or using (2) above and defining k as $$k \triangleq 2\pi f/c = 2\pi/\lambda \quad (\lambda \text{ is the wavelength})$$

the pressure on the x-axis becomes $$p(x) = p_{max} \cdot \cos [kx \cdot \sin a]. \qquad (4)$$

We can now find the voltage generated at each point on the transducer by using the piezoelectric relation $$v = g \cdot p\bot \qquad (5)$$

where v is the voltage, g the piezoelectric coefficient, relating how much voltage is produced for what pressure, and $p\bot$ is the component of the pressure perpendicular to the transducer surface in this case simply cos a times the pressure; therefore, using (4) and (5), $$v(x) = g \cdot p_{max} \cdot \cos a \cdot \cos [kx \cdot \sin a]. \tag{6}$$

The total voltage produced for a beam at angle a by the transducer is the integral of the voltage over the active part of the transducer:

$$V(a) = g \cdot \cos a \cdot p\max \int_{-X_o}^{X_o} \cos[kx \cdot \sin a] dx \tag{7}$$

We have completed the method of finding the voltage from a transducer insonified with a beam at angle a over a total length of $2x_o$. What remains is the mechanics of solving equation 7.

We could solve this numerically with a computer (as we will do with more complicated shapes), but using this flat model we can solve (7) in closed form. This will allow us to validate the computer-generated numerical solutions with the closed-form results.

Solving the Integral

We use the well known relationship $$e^{i\Theta} = \cos \Theta + i \sin \Theta \tag{8}$$

and the fact that the integral of a complex quantity is the sum of the real and imaginary parts, we can rewrite equation 7 as $$V(a) = g \cdot \cos a \cdot p\max \cdot Re \int_{-X_o}^{X_o} e^{-kx\sin a} dx \tag{9}$$

This exponential integral is easily solved as $$\int e^{ax} = \frac{e^{ax}}{a}$$

so (9) becomes $$V(a) = g \cdot \cos a \cdot p\max \cdot \left[ \frac{e^{-ikx \cdot \sin a} e^{-ikx \cdot \sin a}}{ik \sin a} \right] \tag{10}$$

as $\frac{1}{2i}(e^{ix} - e^{-ix}) = \sin x$ as $1/2i (e^{ix} - e^{-ix}) = \sin x$ then $$V(a) = g \cdot \cos a \cdot p_{max} \cdot 2x_o \cdot \text{sinc}(kx_o \sin a) \tag{11}$$

where sinc (x), a tabulated function, is defined as sinc $x = \sin x/x$

We had carefully chosen the reference wavefront to be at maximum pressure at $x=0$. At a different time, as can be seen from eq. 1, we would have zero response; indeed, we would expect to have an oscillating output, at the ultrasonic frequency.

We are interested in the peak signal level. The way we can assure getting the peak signal is to use the absolute value or the integral. That is because the integral can be considered the sum of the vectors in the complex plane, where the argument of the exponential gives the angle and the length of the vector is given by the multiplier of the exponential. When we take the absolute value, we are examining the total length of the sum of the vectors; this total vector would sweep around once per cycle and be equal to the maximum value, as we desire.

So the general approach to the integral such as (9) is $$V(a) = g \cdot \cos a \cdot p\max \cdot \left| \int_{X_{min}}^{X_{max}} e^{-ik\Delta L dx} \right|$$

The Shortcomings of Flat Transducers

We see the pattern plotted in FIG. 2. Of particular note is the zero of response, where the sin is zero:

$$kX_o \sin a = \pm \pi, \pm 2\pi, \ldots$$

The first zero is at $$\frac{2\pi}{\lambda} X_o \sin a = \pi$$

so $\sin a = \lambda/2$   $X_o = \lambda/\text{length of transducer}$

Hence, the response goes to zero at the angle $a = \sin^{-1}$ (wavelength/transducer length)

which gives limited angular response for flat transducers, as is discussed in regard to the patent for the tubiform transducers.

The lack of wide angular response of these flat transducers demands consideration of curved-surface transducers. Before discussing the curved transducer problem, we wish to review the method used.

Recapitulation of the Method

The steps of the method of calculating the response are: Establish the reference wavefront in relation to the transducer; calculate the difference in pathlength from the reference wavefront to the transducer as a function of position on the transducer; convert the pathlength differences to phase differences by multiplying by k; use exponential notation in an integral over the transducer surface to sum the effect of the phase differences over the transducer, with the piezoelectric coefficient to convert the pressure to voltage and the cosine of the angle between the direction of the wavefront and the transducer to account for the component of the pressure in the direction perpendicular to the transducer; take the absolute magnitude of the integral to find the maximum value of the voltage produced.

The Curved Transducer

FIG. 3 shows the reference wavefront and the curved transducer surface. We calculate the pathlength differences as function of position on the transducer surface in two stages: first the pathlength difference to the x-axis, using the results of the flat transducer analysis, and then adjusting the pathlength for the additional path from the x-axis to the transducer.

As shown in the figure, we calculate the pathlength to the point of intersection with the x-axis of the wavefront at angle a to the z-axis of the ray that hits the transducer at the position given by the angle b. Using simple trigonometry, we can calculate the distance L from the origin to the point of intersection in terms of a, b, and r, the radius of curvature of the transducer. From the previous analysis, we know that the pathlength difference is given by L·sin a, for the situation as drawn the phase at the point $x=L$ in advance of the phase at 0. However, this pathlength advantage is reduced by the extra pathlength from A to B.

As shown in FIG. 3, the total pathlength difference, as function of a, b, and r, is $$\Delta = ([\sin a \cdot (r \cdot \tan b) + (m \cdot \cos b \cdot \tan a) - (m \cdot \sin b)] - (m \cdot \cos b / \cos a) \tag{13}$$

where $m = r(1 - \cos b)/\cos b$

We convert that to phase change as before, add the component of the wavefront perpendicular to the surface by subtracting ∠a from ∠b, convert the pressure to voltage by the piezoelectric coefficient g, and integrate, using the differential r·db as is appropriate in cylindrical coordinates. By taking the absolute value we obtain the peak output voltage independent of time:

$$V(a) = g \cdot p\max \cdot \int_{b_{min}}^{b_{max}} \cos(a - b) \cdot e^{ik}\{[\sin a(r \cdot \tan b) + (m \cdot \cos b \cdot \tan a) - (m \cdot \sin b)] - (m \cdot \cos b/\cos a)\} \cdot r \cdot db \tag{14}$$

Doubly-Curved Transducer

The equation above took into account only one axis of curvature; a typical transducer to be mounted on a catheter would be rotationally symmetric, so would have a second radius of curvature.

We show a doubly-curved transducer in FIG. 4. If, for example the Earth were such a doubly curved surface, we would consider a longitude line, say at 0 degrees, as the line we have just calculated the response for, with the source of ultrasound wavefront along that longitude at an angle a to the perpendicular to the equator crossing the 0 longitude.

If we consider the response for the portion of the transducer parallel to the first longitude, i.e. at longitude 10, then the response is the same except that 1) there is a pathlength difference, as shown in FIG. 4(b), of $$\Delta l = r \cdot (1 - \cos e)$$

and there is another adjustment for the component of the angle perpendicular to the transducer surface of cos 3.

We can get the total response by summing all the longitude lines. We do this by taking the voltage for each longitude and integrating. We get a double integral, as we would expect for the response of a surface:

$$V_{tot}(a) = g \cdot p\max \cdot \left| \int_{e_{min}}^{e_{max}} \cos e \cdot e^{ikr2} \cdot \cos e \cdot (1 - \cos e) \cdot \int_{b_{min}}^{b_{max}} \cos(a - b) e^{ik\Delta L} rr2 db de \right|$$

where we use ΔL for the long exponential term in (14).

We can now try different radii of curvature, r for the "longitudinal" curvature and r2 for the "equatorial" curvature, as well a for different angles a of impinging acoustic wavefronts.

These integrals, performed by a computer program (on MathCad, by Mathsoft, Cambridge, Mass., Vers. 2.05) were evaluated for differing degrees of curvature and the results plotted in FIG. 6 of the patent. We chose in this case to pick the radii the same in both directions, i.e. the transducer on the surface of a sphere, but it is clear how either differing radii, or for that matter, non-spherical surfaces (ellipses, etc.) could be carried out by the same general method.

We claim:

1. A transducer for use in conjunction with a scanning ultrasonic imaging system, said system emitting ultrasonic waves at a selected frequency and wavelength into a medium in which ultrasound propagates to enable the location of said transducer and a tubular device associated therewith in said medium, comprising:

an annular member having a central opening for accomodating said tubular device and an outer surface being convex relative to both the axis of said member and to the lines perpendicular to said axis which pass through said member, said convexity relative to either said axis of said member or to said perpendicular lines having a radius of curvature of approximately between 2 to 50 times that of said selected wavelength of said emitted ultrasonic waves.

2. The transducer according to claim 1, wherein said annular member is coated with a piezoelectric material.

3. The transducer according to claim 1, wherein said tubular device is a catheter, said central opening accomodating said catheter which passes therethrough in contact with said member, said transducer affixing to said catheter proximate one end thereof.

4. The transducer according to claim 3, wherein said catheter is a balloon angioplasty catheter.

5. The transducer according to claim 1, wherein said radius of curvature is approximately 6 times that of said selected wavelength when said selected frequency is 7.5 MHz.

6. The transducer according to claim 1 wherein the outer surface comprises a multiplicity of facets that approximate a smooth curved surface.

7. A method used with a scanning ultrasonic imaging system for locating a tubular device directed into a patient's body and moved by a physician to a location of interest in said body, comprising the steps of, securing an annular transducer having a central opening for accomodating said tubular device and an outer surface being convex relative to both the axis of said member and to the lines perpendicular to said axis which pass through said member, said convexity relative to either the axis of said member or to said perpendicular lines having a selected radius of curvature, about said tubular device;

and operating said ultrasonic imaging system to generate ultrasonic waves at a selected frequency such that said selected radius of curvature is between approximately 2 to 50 times that of the wavelength of said ultrasonic waves.

8. The method according to claim 7, wherein said outer surface of said annular transducer has a coating of piezoelectric material and electronic leads extending from said piezoelectric material to said ultrasonic imaging system, and further including the steps of transducing pressure from said ultrasonic waves into an electrical signal with said piezoelectric material coating; conducting said signal along said electronic leads to said system; and monitoring said signal to ascertain the position of said transducer and said catheter.

9. The method according to claim 8, wherein said piezoelectric material is polyvinylidene-diflouride.

10. The method according to claim 7, wherein said selected radius of curvature of said surface is approximately 6 times the wavelength of said ultrasonic waves at a frequency of 7.5 MHz.

11. The transducer according to claim 7, wherein said catheter is a balloon angioplasty catheter.

12. A transducer for use with a scanning ultrasonic imaging system, said system emitting ultrasonic waves at a selected frequency and wavelength in a selected scanning plane in a patient's body for ascertaining the position of said transducer and a catheter associated therewith relative to said patient's body in which said transducer and said catheter have been introduced, comprising:

an annular member having a central opening for accomodating said catheter, an outer surface, a portion of which is convex relative to both the axis of said member and to lines perpendicular to said axis which pass through said member, said convexity relative to either said axis of said member or to said perpendicular lines having a radius of curvature of approximately between 2 to 50 times that of said selected wavelength of said emitted ultrasonic waves.

13. The transducer according to claim 12, wherein said annular member is coated with a piezoelectric material.

14. The transducer according to claim 12, wherein said central opening accomodates said catheter which passes therethrough in contact with said member, said transducer affixing to said catheter proximate one end thereof.

15. The transducer according to claim 14, wherein said catheter is a balloon angioplasty catheter.

16. The transducer according to claim 12, wherein said radius of curvature is approximately 6 times that of said selected wavelength when said selected frequency is 7.5 MHz.

17. The transducer according to claim 12, wherein only a portion of the surface of said transducer is coated with a piezoelectric material.

18. The transducer according to claim 12, wherein said annular member is asymmetrical in shape.

19. The transducer according to claim 12, wherein said annular member is elliptical in shape.

20. A transducer for use in conjunction with a scanning ultrasonic imaging system, said system emitting ultrasonic waves at a selected frequency and wavelength into a medium in which ultrasound propagates, to enable the location of said transducer and a tubular device associated therewith within said medium, comprising:

a toroidal member having a central opening for accomodating said tubular device and a doubly convex outer surface, at least a portion of the parallels and at least a portion of the meridians of said outer surface having a radius of curvature of approximately 2 to 50 times the wavelength of the ultrasonic waves employed by said scanning ultrasonic imaging system.

* * * * *